(12) United States Patent
Xu et al.

(10) Patent No.: US 7,393,990 B2
(45) Date of Patent: Jul. 1, 2008

(54) PRODUCTION OF LIGHT OLEFINS FROM OXYGENATE USING FRAMEWORK GALLIUM-CONTAINING MEDIUM PORE MOLECULAR SIEVE

(75) Inventors: Teng Xu, Houston, TX (US); Jeffrey L. White, Cary, NC (US); Xiaobing Feng, Houston, TX (US); Gary D. Mohr, Houston, TX (US); Brenda A. Raich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/892,307

(22) Filed: Jun. 26, 2001

(65) Prior Publication Data
US 2003/0018231 A1 Jan. 23, 2003

(51) Int. Cl.
*C07C 1/20* (2006.01)
*C07C 1/207* (2006.01)

(52) U.S. Cl. .................................. 585/640; 585/639

(58) Field of Classification Search ............ 585/634, 585/640
See application file for complete search history.

(56) References Cited

U.S. PATENT DOCUMENTS

| | | | |
|---|---|---|---|
| 3,702,886 A * | 11/1972 | Argauer et al. ........... 423/705 |
| 3,847,756 A | 11/1974 | Statman et al. ............ 203/92 |
| 4,025,575 A | 5/1977 | Chang et al. .............. 260/682 |
| 4,038,889 A | 8/1977 | Lindow et al. ............. 74/866 |
| 4,079,095 A | 3/1978 | Givens et al. ............. 260/682 |
| 4,311,865 A | 1/1982 | Chen et al. ................ 585/640 |
| 4,350,835 A | 9/1982 | Chester et al. ............ 585/415 |
| 4,474,647 A | 10/1984 | Asselineau et al. ......... 203/49 |
| 4,499,314 A | 2/1985 | Seddon et al. ............. 585/408 |
| 4,605,805 A | 8/1986 | Chang et al. .............. 585/415 |
| 4,638,106 A * | 1/1987 | Pieters et al. ............. 585/408 |
| 4,677,242 A | 6/1987 | Kaiser ..................... 585/638 |
| 4,752,651 A | 6/1988 | Kaiser ..................... 585/640 |
| 4,822,939 A | 4/1989 | Chu ........................ 585/408 |
| 4,861,938 A * | 8/1989 | Lewis et al. ............... 208/107 |
| 5,023,391 A | 6/1991 | Han et al. ................. 585/500 |
| 5,037,511 A | 8/1991 | Dornhagen et al. .......... 203/37 |
| 5,122,236 A | 6/1992 | Smith, Jr. et al. ........... 203/43 |
| 5,460,796 A | 10/1995 | Verduijn .................. 423/700 |
| 5,763,712 A | 6/1998 | Roth et al. ................ 570/258 |
| 5,843,286 A | 12/1998 | Roth et al. ................ 203/18 |
| 5,882,485 A | 3/1999 | Roth et al. ................ 203/14 |
| 5,962,762 A | 10/1999 | Sun et al. ................. 585/640 |
| 5,981,817 A | 11/1999 | Kao et al. ................. 585/481 |
| 6,150,293 A * | 11/2000 | Verduijn et al. ............ 502/63 |

OTHER PUBLICATIONS

Inui, I., "Structure-Reactivity Relationships in Methanol to Olefins Conversion in Various Microporous Crystalline Catalysts," *Structure-Acitivity and Selectivity Relationships in Heterogeneous Catalysis*, Elsevier Science Publisher, B.V. Amsterdam (1991), pp. 233-242.
Mole, T., et al, "Conversion of Methanol to Hydrocarbons over ZSM-5 Zeolite: An Examination of the Role of Aromatic Hydrocarbons Using [13]Carbon-and Deuterium-Labeled Feeds," *Journal of Catalysis*, vol. 84, (1983), pp. 435-445.

* cited by examiner

*Primary Examiner*—Thuan Dinh Dang

(57) ABSTRACT

A method is provided for converting oxygenates, e.g., methanol, to olefins, e.g., ethylene and propylene, comprising contacting said oxygenates and an aromatics co-feed, e.g., xylenes, with a framework gallium-containing molecular sieve catalyst comprising pores having a size ranging from about 5.0 Angstroms to about 7.0 Angstroms, e.g., ZSM-5, under production conditions effective to produce olefins. A catalyst composition is also provided, comprising a ZSM-5 zeolite-bound ZSM-5 zeolite having a bound zeolite of framework Ga-containing zeolite having a Si/Ga molar ratio ranging from 5 to 500 and a binder of Ga-modified, e.g., Ga-exchanged and/or Ga-impregnated, zeolite having a Si/Ga molar ratio ranging from 5 to ∞.

5 Claims, No Drawings

PRODUCTION OF LIGHT OLEFINS FROM OXYGENATE USING FRAMEWORK GALLIUM-CONTAINING MEDIUM PORE MOLECULAR SIEVE

BACKGROUND OF THE INVENTION

1. Field of the Invention

The present invention relates to a method for converting oxygenate, such as methanol and/or dimethyl ether, to olefins in a reactor over a framework gallium-containing medium pore molecular sieve catalyst such as ZSM-5 or ZSM-11 wherein oxygenate can be co-fed with aromatics. The method is especially useful for increasing ethylene/propylene product ratio.

2. Description of the Background Art

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, as well as four and five carbon olefins. Along with this growth has been an increasing demand for alkylate, made by reacting olefins with isobutane, for use as a high octane gasoline component.

Burgeoning demand for olefins, particularly ethylene, propylene and butenes, has of course led to periods of shortage, causing substantial price increases in the feedstocks to various commercialized technologies. These feedstocks are largely $C_2$ to $C_4$ paraffins co-produced with natural gas and/or paraffinic straight run naphtha. Such feedstocks can be substantially more expensive than methane, making it desirable to provide efficient means for converting methane to olefins.

Conversion of methane to methanol followed by conversion of methanol to light olefins is among the most economic routes to make light olefins from methane. In this respect, it is known that methanol or dimethyl ether can be catalytically converted to olefin-containing hydrocarbon mixtures by contacting under certain conditions with particular types of crystalline zeolite materials. U.S. Pat. Nos. 4,025,575 and 4,038,889, for example, both disclose processes whereby methanol and/or dimethyl ether can be converted to an olefin-containing product over a Constraint Index 1-12 zeolite catalyst, particularly ZSM-5. In fact, ZSM-5 converts methanol and/or dimethyl ether to hydrocarbons containing a relatively high concentration of light olefins with prolonged catalyst lifetime before catalyst regeneration becomes necessary. U.S. Pat. No. 4,311,865 teaches the use of the medium pore zeolite, ZSM-5 (approximately 5.5 Angstroms) pore size, which is ion-exchanged with cobalt, and then calcined to produce a catalyst, and has been used to convert methanol to hydrocarbons (including olefins). This process uses ion-exchange to add the metal to the medium pore molecular sieve. Despite the durability of these medium pore size catalysts, they exhibit a low selectivity for ethylene when converting oxygenates. For example, HZSM-5 can exhibit ethylene selectivity of less than 5%.

It has also been reported that other types of zeolite catalysts can be used to convert methanol and/or dimethyl ether to olefin-containing hydrocarbons products containing higher proportions of light olefins than previously obtained with ZSM-5. For example, U.S. Pat. No. 4,079,095 discloses that zeolites of the erionite-offretite-chabazite type, and especially ZSM-34, can promote conversion of methanol and/or methyl ether to products comprising a major amount of ethylene and propylene. However, while erionite-offretite-chabazite type catalysts are highly selective to light olefins production, such smaller pore zeolites tend to age rapidly in comparison to ZSM-5 when used for methanol/dimethyl ether conversion, perhaps owing to the rapid buildup of coke inside the zeolite cages, which blocks the accessibility of methanol feed to the acid sites contained therein. Small pore catalysts such as SAPO-34 have been used to convert methanol to olefins, as described in an article by T. Inui, "Structure-Reactivity Relationships in Methanol to Olefins Conversion in Various Microporous Crystalline Catalysts, Structure-Activity and Selectivity Relationships in Heterogeneous Catalysts", pages 233-42, Elsevier Science Publishers, B. V., Amsterdam (1991). U.S. Pat. No. 5,962,762 to Sun et al. discloses a method for converting starting material to olefins comprising contacting the starting material with a small pore molecular sieve catalyst such as SAPO-34 under effective conditions to produce olefins, wherein the molecular sieve has been modified after synthesis by incorporation of a transition metal ion using a transition metal compound, wherein the transition metal ion is selected from Groups VIB, VIIB, and VII.

T. Mole, G. Bett, and D. J. Seddon, Journal of Catalysis 84, 435 (1983), disclose that the presence of aromatic compounds can accelerate the zeolite-catalyzed conversion of methanol to hydrocarbons. The article reports ethylene yields of 5-22% when methanol is catalytically converted in the presence of benzene or toluene over ZSM-5 at sub-atmospheric pressure, 279° to 350° C., and 100% methanol conversion. U.S. Pat. No 4,499,314 ('314 Patent) discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 Patent teaches that the increased conversion resulting from the addition of the promoter allows the use of lower severity conditions, particularly lower temperatures, which increase the yield of lower olefins (column 4, lines 17-22). Thus, in Example 1 of the patent the addition of toluene as a promoter reduces the temperature required to achieve full methanol conversion from 295° C. to 288° C. while increasing the ethylene yield from 11 wt. % to 18 wt. %. In the Examples of the '314 patent the methanol feedstock is diluted with water and nitrogen such that the methanol partial pressure is less than 2 psia (14 kPa). U.S. Pat. Nos. 4,677,242 and 4,752,651 disclose the conversion of methanol to $C_2$ to $C_4$ olefins over various silicoaluminophosphates such as SAPO-34, and "non-zeolitic molecular sieves" (such as metal aluminophosphates), and teach that the addition of diluents, such as aromatic materials, having a kinetic diameter greater than the pore size of the molecular sieve, increases the ethylene to propylene ratio in the product.

Conversion of ethane to aromatics over GaZSM-5 is disclosed in U.S. Pat. No. 4,350,835. U.S. Pat. No. 4,605,805 discloses a catalyst for olefin/paraffin conversion that employs ZSM-5 having a framework wherein gallium is substituted for boron or iron. U.S. Pat. No. 5,023,391 discloses a process for the direct partial oxidation of methane with oxygen, whereby organic compounds comprising higher hydrocarbons are produced. The catalyst used in this reaction is a GaZSM-5 catalyst. This catalyst may be prepared by ion exchanging or impregnating a ZSM-5 catalyst with a suitable gallium salt such as gallium nitrate.

U.S. Pat. No. 5,981,817 discloses a xylene isomerization process conducted in the presence of hydrogen and at pressures in excess of 75 psig (620 kPa) over a ZSM-5 catalyst containing about 0.1 to 5 wt. % of at least one metal selected from the group consisting of zinc, copper, silver and gallium. The catalyst may be a zeolite bound zeolite prepared in accordance with U.S. Pat. No. 5,460,796.

All of the foregoing references are incorporated herein by reference.

In spite of the existence of methanol conversion processes utilizing a variety of zeolite catalysts and process conditions, there is a continuing need to develop new procedures suitable to convert an organic feed comprising oxygenates, such as methanol or dimethyl ether, selectively to light olefin products and, in particular, ethylene.

SUMMARY OF THE INVENTION

In one aspect, the present invention relates to a method for converting oxygenates to olefins comprising contacting said oxygenates and an aromatics co-feed with a framework gallium-containing molecular sieve catalyst comprising pores having a size ranging from about 5.0 Angstroms to 7.0 Angstroms, under conversion conditions effective to produce olefins.

The method is especially useful in providing products of relatively high ethylene/propylene ratio on a weight basis.

In another aspect, the present invention relates to a method for converting methanol and/or dimethyl ether to a product containing $C_2$ and $C_3$ olefins which comprises the step of contacting a feed which contains methanol and/or dimethyl ether with a catalyst comprising a framework gallium-containing ZSM-5 porous crystalline material, said contacting step being conducted in the presence of an aromatic compound under conversion conditions including a temperature of 100° C. to 600° C. and a methanol and/or dimethyl ether partial pressure in excess of 1 psia (6.9 kPa), and the aromatic compound being capable of alkylation by the methanol and/or dimethyl ether, under said conversion conditions.

In still another aspect, the present invention relates to a catalyst composition comprising a gallium-containing ZSM-5 zeolite-bound ZSM-5 zeolite comprising a bound ZSM-5 zeolite with framework Ga of Si/Ga molar ratio ranging from 5 to 500 and a ZSM-5 zeolite binder having a Si/Ga molar ratio ranging from 5 to ∞. The catalyst composition may comprise a component in which gallium has been introduced by secondary synthesis or post-synthesis modification, i.e., the catalyst composition may comprise at least one component selected from the group consisting of bound Ga-modified ZSM-5 zeolite having a Si/Ga molar ratio ranging from 5 to 500 and a binder of Ga-modified ZSM-5 zeolite having a Si/Ga molar ratio ranging from 5 to ∞.

Gallium in the bound zeolite component of the catalyst is preferably introduced to the framework of the molecular sieve during its synthesis. Gallium can be preferably introduced into the binder through a secondary synthesis. The catalyst of the present invention may also be prepared using post zeolite synthesis gallium modification. Such gallium modified materials have been subjected to ion-exchange or wet impregnation, to the extent that such techniques provide framework gallium in the finished catalyst. Thus, it is also possible that some of the Ga in the catalyst may be present as non-framework species, e.g., as a result of calcination.

DETAILED DESCRIPTION OF THE INVENTION

It is known to selectively convert oxygenates, including methanol, to light olefins, viz., ethylene ($C_2^=$) and propylene ($C_3^=$). Ethylene and propylene are in high demand, and the need for these chemical raw materials, particularly ethylene, continues to grow. In the present invention, oxygenate, e.g., oxygenate selected from the group consisting of methanol and dimethylether, is reacted at elevated temperature over a bed of a framework gallium-containing, medium pore molecular sieve catalyst, e.g., GaZSM-5, to produce a reaction product from which lower ($C_2$ and $C_3$) olefins are recovered.

Catalyst

Crystalline aluminosilicates which may be used as molecular sieve material for the catalyst of the present invention include intermediate pore size zeolites having an average pore size in the range of about 5 to 7 Angstroms and a $SiO_2/M_2O_3$ ratio of at least 10, where M represents an element selected from the group consisting of Al, B, Fe, Ga, V, and Cr.

These include zeolites having an MFI, MEL, TON, MTT or FER crystalline structure. Preferred such zeolites include those selected from the group consisting of ZSM-5, ZSM-11, ZSM-12, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described in U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. MCM-22 is disclosed in U.S. Pat. No. 4,954,325, U.S. Pat. No. 5,304,698, U.S. Pat. No. 5,250,277, U.S. Pat. No. 5,095,167, and U.S. Pat. No. 5,043,503.

The zeolite is advantageously ion-exchanged so as to be in its highly acidic form, e.g., HZSM-5. Where the zeolite, as synthesized, contains alkali or alkaline earth metal cations, these can be exchanged with ammonium cations, followed by calcination in air at 600° F. to 1000° F. (316° C. to 540° C.) for about 1-10 hours by techniques well known in the art to produce the acid form of the zeolite.

Silicoaluminophosphates such as SAPO-34, and "non-zeolitic molecular sieves" (such as metal aluminophosphates) as described in U.S. Pat. Nos. 4,677,242 and 4,752,651 can be treated with gallium and used in the present invention.

The gallium loaded into the catalyst appears to limit the extent of coking in the catalyst during conversion of oxygenate to olefins, providing increased service life. The gallium may be incorporated into the zeolite framework structure by any suitable method of isomorphous substitution, e.g., substituting Ga atoms for framework aluminum atoms. Alternatively, Ga can be present in the as-synthesized zeolite by including Ga-containing materials in the synthesis mixture, preferably before exposure of the synthesis mixture to hydrothermal conditions. Gallium may also be introduced inside and/or outside the framework of the molecular sieve by well known post-synthesis gallium modification methods such as impregnation (incipient wetness method) or by gallium ion exchange (gallium exchange). Thus in one aspect of the present invention, the zeolite can be impregnated with a source of gallium by well known methods such as by contacting a solution of gallium salt dissolved in an aqueous or alcoholic medium with the zeolite particles for a period of time sufficient to allow the cations to penetrate the zeolite pore structure. Suitable salts include the acetates, chlorides and nitrates. After drying the resulting catalyst precursor, it is preferably calcined in air at temperatures of 300° F.-1000° F. (149° C.-540° C.) for a period of 1-24 hours. In most cases, the metal will be present in the post-calcined zeolite structure in the form of the metal oxide. The preferred metal loading ranges from about 0.01 to about 10 wt. %, more preferably from about 0.1 to 2.5 wt. % metal based on the weight of the zeolite.

The gallium impregnation or exchange process described above may be carried out before or after the porous crystalline material is composited with the binder, but preferably before.

The porous crystalline material employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst and hence is generally not preferred. Inactive materials suitably serve as diluents to control the amount of conversion in a given process so that products can be obtained in an economical and orderly manner without employing other means for controlling the rate of reaction. These materials may be incorporated into naturally occurring clays, e.g., bentonite and kaolin, to improve the crush strength of the catalyst under commercial operating conditions. These materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst. Naturally occurring clays which can be composited with the porous crystalline material include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite. Preferably, the binder material comprises silica or a kaolin clay. Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process. The porous crystalline material may be combined with a binder in the form of a fluidized bed catalyst. This fluidized bed catalyst may comprise clay in the binder thereof, and may be formed by a spray-drying process to form catalyst particles having a particle size of 20-200 microns.

In one aspect of the present invention, porous crystalline materials comprise a zeolite in the form of zeolite-bound particles such those prepared in accordance with U.S. Pat. No. 5,460,796, the disclosure of which is incorporated herein by reference. In such cases where the catalyst is a zeolite bound zeolite (ZBZ), it can have a bound zeolite of Si/Ga molar ratio ranging from 5 to 500, preferably from 20 to 200 most preferably from 30 to 100, and a binder having a Si/Ga molar ratio ranging from 5 to ∞, preferably from 20 to ∞, most preferably from 100 to ∞. In one embodiment, the catalyst can be a zeolite bound zeolite having a bound zeolite of framework Ga-containing zeolite having a Si/Ga molar ratio ranging from 5 to 500, more preferably from 20 to 200, and most preferably from 30 to 100 and a binder of Ga-exchanged and/or Ga-impregnated zeolite having a Si/Ga molar ratio ranging from 5 to ∞, more preferably from 20 to ∞ and most preferably from 100 to ∞.

The catalyst employed of the invention preferably has a very low acid activity. Using the alpha test of acid activity disclosed in Journal of Catalysis, volume 61, page 395 (1980), the entire disclosure of which is incorporated by reference herein, the catalyst of the invention preferably has an alpha value less than 10, more preferably less than 5, and most preferably less than 2.

Feed

The feed employed in the present invention comprises an oxygenate component. Such oxygenates can be selected from the group consisting of methanol, ethanol, n-propanol, isopropanol, $C_4$-$C_{20}$alcohols, methyl ethyl ether, di-methyl ether, di-ethyl ether, di-isopropyl ether, methyl isopropyl ether, ethyl isopropyl ether, di-methyl carbonate, carbonyl compounds, and mixtures thereof. Preferred oxygenates are selected from the group consisting of methanol and dimethyl ether, with methanol being especially preferred.

An aromatics co-feed is added to the feed of the present invention. Non-limiting examples of such aromatics which comprise aromatic compounds which can diffuse into channels or cages of said catalyst together with oxygenate, can be selected from the group consisting of benzene, toluene, xylenes, light reformates, full-range reformates or any distilled fraction thereof, coker naphtha or any distilled fraction thereof, FCC naphtha or any distilled fraction thereof, steam crack naphtha or any distilled fraction thereof and coal derived aromatics.

Aromatics co-feed selected from the group of aromatic compounds consisting of toluene and xylenes is especially preferred. In one embodiment of the invention, the aromatics co-feed can be added to the feed upstream of the reactor.

Minor amounts, say, 0.01-10 wt. %, of aromatics such as benzene, toluene, and/or xylenes, etc. can be co-fed with the oxygenate in order to enhance olefin selectivity. The aromatics component can be added relative to the oxygenate, e.g., methanol and/or dimethyl ether, in an amount sufficient to provide a feed having a molar ratio of oxygenate to aromatic compound greater than 0.1:1 and less than 300:1, preferably greater than 2:1 and less than 150:1, and more preferably greater than 5:1 and less than 50:1.

In one aspect of the invention, the co-fed aromatic may consist only of the xylene isomers, or may be a mixture of the xylene isomers with another aromatic hydrocarbon such as ethylbenzene, benzene, toluene, ethyltoluene, trimethylbenzene, diethylbenzene, ethylxylene, and tetramethylbenzene. In the latter case, the xylene isomeric mixture is present desirably in an amount of generally at least 30% by weight, preferably at least 50% by weight, based on the weight of the aromatic hydrocarbon feed.

$C_8$ aromatic hydrocarbon fractions obtained by reforming, thermal cracking or hydrocracking of naphtha can be used as the aromatic hydrocarbon additive to the oxygenate feed in the process of this invention. These fractions contain ethylbenzene of the same number of carbons in addition to the xylene isomers. Very good results can be obtained in the process of this invention when using a $C_8$-aromatic hydrocarbon fraction which contains the xylene isomers and ethylbenzene in a total amount of at least 80%.

The present method can be conducted in the presence of added diluent, e.g., hydrogen and/or added water such that the molar ratio of diluent to oxygenate in the feed to the reactor is between about 0.01 and about 10, preferably between about 0.01 and 5, and more preferably between about 0.01 and 2. Those skilled in the art will be capable of adjusting the various reaction parameters and conditions to optimize conversion, yield, and selectivity, using routine experimentation.

Reaction Conditions

The process of the invention is preferably carried out in a moving or fluid catalyst bed with continuous oxidative regeneration. The extent of coke loading can then be continuously controlled by varying the severity and/or the frequency of regeneration. The conversion of oxygenate to olefin according to the present invention may occur in a reactor of any configuration. Continuous reactors, such as dense fluidized bed, riser, fast fluid-bed, or fixed bed, are suitable configurations for use in the present invention. The process of the invention is preferably carried out in a moving or fluid catalyst bed with continuous oxidative regeneration. The extent of coke loading can then be continuously controlled by varying the severity and/or the frequency of regeneration.

Preferably, the reactor is a fluidized bed flow reactor type. The catalyst may be used in various forms, such as a fixed bed, moving bed, fluidized bed, e.g., a dense fluid bed, in suspension in the generally gaseous reaction mixture.

The fluidized beds used in the present invention can be relatively dense, such as turbulent sub-transport fluid beds with an operating bed density of about 200 to 700 kg/m$^3$, preferably about 300 to 500 kg/m$^3$. The use of these dense beds increases the catalyst concentration at the area of oxygenate injection.

A suitable alternate fluid bed design is termed a fast fluid bed. This is typically characterized by a bed density that is lower than that prevailing in a dense fluid bed. Superficial gas velocities are typically greater than 5 feet/second (1.5 meters/second). The fluidized bed in a fast fluid bed is less defined than that in a dense fluid bed.

Another suitable reactor system is a riser "fluid bed" reactor. In this case the classical fluidized bed does not exist but rather solid catalyst particles and gas are flowed up or down the reactor vessel in a more or less homogeneous manner. Typically solids density in the riser is less than about 100 kg/m$^3$, and the superficial gas velocity is in excess of 20-40 feet/second (6-12 meters/second).

Liquids can be injected into all three types of fluid bed systems mentioned above.

The catalyst inventory of the fluidized beds can be maintained by return of solids to the beds from the cyclone recovery system, but small losses will occur, e.g., due to attrition. Losses can be made up by adding catalyst to maintain catalyst inventory.

The production conditions of the present invention can comprise a temperature of from about 100° C. to about 600° C., a pressure of from about 1 psia to 200 psia (6.9 kPa to 1380 kPa), and a weight hourly space velocity in the range of from about 0.01 to about 500 hr$^{-1}$, preferably a temperature of 350° C. to 480° C., a pressure of from about 5 psia to 100 psia (34 kPa to 680 kPa), and a weight hourly space velocity in the range of from about 2 to about 100 hr$^{-1}$.

These conditions can be effective to provide an ethylene/propylene product weight ratio ranging from 0.1 to 7, preferably at least 1. Combinations of temperatures of 250° to 480° C. and ethylene/propylene product weight ratio ranging from 0.1 to 7, and preferably 300° to 450° C. and ethylene/propylene product weight ratio of at least 1, can be used.

Operating at higher oxygenate, e.g., methanol and/or dimethylether, partial pressures can allow the absolute yield per pass of olefin product to be increased. A suitable methanol and/or dimethylether partial pressure for use in the process of the invention is in excess of 10 psia (70 kPa), preferably 15 to 150 psia (103 to 1030 kPa).

The present invention can employ oxygenate conversion levels of greater than 95%, greater than 98% or even greater than 99%, e.g., 100%.

Suitable control of the oxygenate, e.g., methanol, conversion can, of course, be achieved by variation of the weight hourly space velocity, which typically can vary between about 0.1 and 100, preferably between about 0.1 and 10. The process of the invention can convert oxygenate, e.g., methanol and/or dimethyl ether to a light olefin-containing stream with ethylene selectivity of at least 25%, preferably at least 40%, and propylene selectivity of at least 30%, preferably at least 40% as well as an ethylene/propylene ratio of greater than 0.6, preferably greater than about 1. Such high selectivities for lower olefins can be achieved even at high oxygenate conversions, e.g., greater than 99%.

The following examples are provided to more fully illustrate the invention and accent its advantageous features. These examples are included to illustrate the invention and should not be construed as limiting it in any way.

EXAMPLE 1

Catalyst Preparation

A gallium-substituted zeolite bound zeolite, ZSM-5, i.e., H(Ga)ZSM-5, was prepared in accordance with the details provided below:

1. Preparation of the crystals to be bound having a $SiO_2/Ga_2O_3$ Ratio of 90 and a crystal size of approximately 3 microns:

This was carried out by a procedure similar to Example 1 of U.S. Pat. No. 6,040,259, incorporated herein by reference. The synthesis mixture consisted of the following parts (by weight):

Part A: NaOH, $Ga_2O_3$ (99.999 wt. %) and water were used to make a solution by boiling the ingredients and cooling to room temperature, about 25° C. Water lost during boiling was replaced.

Part B: Colloidal silica in water.

Part C: Tetrapropylammonium Bromide (TPABr) and water.

Part D: MFI (ZSM-5) seeds.

Part B was added to Part C and mixed. Then Part D was added. Finally Part A was added and mixed until the resulting mixture was homogeneous. The final reaction mixture had the following composition:

0.45 $Na_2O$/0.9 TPABr/0.111 $Ga_2O_3$/10 $SiO_2$/147 $H_2O$ and 1.4 wt ppm of MFI seeds. The final reaction mixture was heated to 140° C. for about 24 hrs and the resulting powder was washed, dried and calcined.

2. Preparation of silica bound crystals in a ratio of bound zeolite/binder of 70/30:

A mixture was made and extruded according to U.S. Pat. No. 5,460,796, incorporated herein by reference, Example 1, Step B. The resulting extrudates were calcined.

3. Preparation of GaMFI bound GaMFI (secondary synthesis):

Part A: calcined silica bound GaMFI prepared under Step 2 above.

Part B: solution containing NaOH, $Ga_2O_3$, TPABr and water.

Parts A and B were combined and the resulting mixture had the following overall composition: 0.48 $Na_2O$/0.7 TPABr/ 0.05 $Ga_2O_3$/10 $SiO_2$/149 $H_2O$ exclusive of the GaMFI crystals.

The 10 moles of $SiO_2$ are the binder of the extrudates. The mixture is heated at 150° C. for 80 hrs to convert the binder to GaMFI (GaZSM-5).

4. Calcination and Ion Exchange:

The resulting extrudates of Step 3 were washed, dried, and calcined. Then the extrudates were ion-exchanged with $NH_4NO_3$ and calcined to obtain the final catalyst.

The bound zeolite of the catalyst had a Si/Ga ratio of about 45 while that of the binder was about 100. The catalyst was calcined at 450° C. in air overnight prior to use.

Light Olefins Production

The production of light olefins was carried out by mixing 50.0 mg of a selected Ga-containing catalyst prepared following steps 1-4 in Example 1, with 1.0 gram of silicon carbide. The resulting mixture was then placed in a 0.50 inch (1.3 cm) (outside diameter) No. 304 stainless steel tubular reactor having a wall thickness of 0.063 inch (0.16 cm). A thermocouple was provided in direct contact with the catalyst for temperature measurements. The catalyst was activated in situ by heating in flowing helium for one hour at 450° C. in the reactor.

Feedstock comprising methanol and aromatics co-feed was introduced to the tubular reactor by means of a Valco four-port injection valve with a fixed volume of 3 l concurrently with a stream of helium diluent. The pressure and temperature employed in this Example were 40 psia (275 kPa) and 450° C., respectively. The effluent from the tubular reactor following each pulse of methanol was collected using a Valco six-port valve with a 2 ml sample loop. The collected effluent sample was analyzed by gas chromatography (Hewlett Packard 6890) equipped with a flame ionization detector. The chromatographic column used was a 150 meter, 0.25 mm (i.d.) fused silica capillary column (Model No. Petrocol DH 150).

In calculating selectivities reported in Table 2 to Table 7, dimethyl ether is not counted as one of the converted products from methanol, i.e., dimethyl ether is treated as if it were methanol. Nor are toluene, xylenes and other alkylated aromatics that are produced from methanol counted as converted products because these aromatics are recycled.

Tables 1-6 below set out product distributions (wt. %) and ethylene to propylene molar ratios for methanol and methanol/aromatic feeds of Examples 2-7.

EXAMPLE 2 (Comparative)

Pure methanol feed was reacted on H(Ga)ZSM-5 from Example 1 as a control for a para-xylene co-feed experiment at 100 wt. % MeOH conversion. The product distributions (wt. %) and ethylene to propylene molar ratio are listed in Table 1 below. $C_3^0$ and $C_4^0$ refer to propane and butane while $C_2=$ and $C_3=$ refer to ethylene and propylene.

TABLE 1

| $CH_4$ | $C_2=$ | $C_3=$ | $C_3^0$ | $C_4^0$ | $C_4=$ | $C_5=$ | $C_2=/C_3=$ |
|---|---|---|---|---|---|---|---|
| 0.5 | 5.9 | 49.8 | 0.3 | 1.1 | 24.0 | 12.5 | 0.12 |

EXAMPLE 3

A mixture of 50/50 wt. % of methanol and para-xylene is reacted in the presence of H(Ga) ZSM-5 under the same conditions as in Comparative Example 2. The results set out in Table 2 below show an increase in the total ethylene and propylene selectivity of 77.5 wt. % compared to Example 2's 55.7 wt. %).

The selectivity to ethylene is higher than that of propylene, in contrast to Comparative Example 2 where the selectivity to ethylene was negligible.

TABLE 2

| $CH_4$ | $C_2=$ | $C_3=$ | $C_3^0$ | $C_4^0$ | $C_4=$ | $C_5=$ | $C_2=/C_3=$ |
|---|---|---|---|---|---|---|---|
| 3.8 | 44.0 | 33.5 | 1.5 | 0.5 | 11.1 | 5.6 | 1.31 |

EXAMPLE 4

A mixture of 90/10 wt. % of methanol and para-xylene is reacted in the presence of H(Ga) ZSM-5 under the same conditions as in Example 2. The results in Table 3 show a high selectivity to ethylene and propylene (65.7 wt. %) is maintained. Although the ethylene to propylene ratio is lower than that in Example 3, in some embodiments such lower ratio is preferred. Despite ethylene's higher value as a commodity than propylene, there are occasions where high propylene selectivity is desired. This experiment shows that ethylene to propylene ratio can be varied by simply adjusting the amount of aromatics in the feed.

TABLE 3

| $CH_4$ | $C_2=$ | $C_3=$ | $C_3^0$ | $C_4^0$ | $C_4=$ | $C_5=$ | $C_2=/C_3=$ |
|---|---|---|---|---|---|---|---|
| 1.7 | 21.4 | 44.3 | 1.6 | 1.0 | 19.5 | 10.4 | 0.48 |

EXAMPLE 5

A mixture of 10/90 wt. % of methanol/para-xylene was reacted on the H(Ga)ZSM-5 catalyst of Example 1 under the same conditions as in Example 2. The results in Table 4 show high selectivity to ethylene and propylene (89.8 wt. %) with very high ethylene selectivity (72.7 wt. %).

TABLE 4

| $CH_4$ | $C_2=$ | $C_3=$ | $C_3^0$ | $C_4^0$ | $C_4=$ | $C_5=$ | $C_2=/C_3=$ |
|---|---|---|---|---|---|---|---|
| 3.1 | 72.7 | 17.1 | 0.5 | 0.0 | 4.3 | 2.3 | 4.25 |

EXAMPLE 6 (Comparative)

The performance of an HZSM-5 catalyst with a $SiO_2$/$Al_2O_3$ ratio of 218 prepared in accordance with Example 1A of U.S. Pat. No. 5,460,796 was studied in the pulse reactor for the co-feeding experiment using a 50/50 wt. % mixture of methanol/p-xylene at 64 wt. % methanol and dimethyl ether (DME) conversion. The results shown in Table 5 below indicate a significant decrease in total ethylene and propylene selectivity (70.3 wt. %) at 64 wt. % conversion compared with H(Ga)ZSM-5 in Example 3 (77.5 wt. %) at 100 wt. % conversion. $C_2=/C_3=$ product ratio is also improved for the present invention (1.31 vs. 0.77).

TABLE 5

| $CH_4$ | $C_2=$ | $C_3=$ | $C_3^0$ | $C_4^0$ | $C_4=$ | $C_5=$ | $C_2=/C_3=$ |
|---|---|---|---|---|---|---|---|
| 2.5 | 30.5 | 39.8 | 0.5 | 0.0 | 16.0 | 10.7 | 0.77 |

EXAMPLE 7

The effect of temperature on olefin selectivities was studied by co-feeding toluene with methanol on H(Ga)ZSM-5 as prepared in Example 1 at 100 wt. % methanol conversion. The results are summarized in Table 6 below.

The reaction temperature has a significant effect on olefin selectivity. As temperature is increased, the ethylene and propylene selectivity increases as well, inasmuch as the thermodynamics favor lighter products. However, at higher temperatures methane selectivity increased significantly. For example, the selectivity for methane was as high as 33.2 wt. % at 550° C. Accordingly, it is preferred that the temperature range be in the range of 100 to 600° C., preferably in the range of 250 to 480° C., more preferably in the range of 300 to 450° C., where methane make is to be minimized.

TABLE 6

| T (° C.) | $CH_4$ | $C_2=$ | $C_3=$ | $C_3^0$ | $C_4^0$ | $C_4=$ | $C_5=$ |
|---|---|---|---|---|---|---|---|
| 400 | 0.5 | 40.1 | 33.5 | 2.3 | 0.8 | 12.7 | 6.5 |
| 450 | 2.4 | 49.7 | 30.0 | 1.9 | 0.3 | 9.7 | 4.8 |
| 500 | 18.9 | 50.2 | 20.7 | 0.8 | 0.2 | 6.1 | 2.9 |
| 550 | 33.2 | 44.7 | 15.0 | 0.3 | 0.1 | 4.2 | 2.0 |

While the invention has been described herein in terms of various preferred embodiments, those skilled in the art will recognize that various changes and modifications can be made without departing from the spirit and scope of the invention, as defined in the following claims.

What is claimed is:

1. A method for converting methanol and/or dimethyl ether to a product containing $C_2$ and $C_3$ olefins which comprises contacting a feed which contains methanol and/or dimethyl ether with a catalyst comprising a gallium-modified ZSM-5 porous crystalline material, said contacting step being conducted in the presence of an aromatic compound under conversion conditions including a temperature of 350° C. to 450° C. and a methanol and/or dimethyl ether partial pressure in excess of 6.9 kPa, and the aromatic compound being capable of alkylation by the methanol and/or dimethyl ether under said conversion conditions wherein said catalyst comprises zeolite-bound zeolite having at least one component selected from the group consisting of bound Ga-modified zeolite having a Si/Ga molar ratio ranging from 5 to 500 and a binder of Ga-modified zeolite having a Si/Ga molar ratio ranging from 5 to ∞.

2. The method of claim 1 wherein the molar ratio of oxygenate to aromatic compound is greater than 0.1:1 and less than 300:1.

3. The method of claim 1 wherein said conversion conditions further comprise a a pressure of from excess of 6.9 to 1380 kPa, and a weight hourly space velocity in the range of from about 0.01 to about 500 $hr^{-1}$.

4. The method of claim 1 wherein said conversion conditions further comprise a a pressure of from 34 to 680 kPa, and a weight hourly space velocity in the range of from about 2 to about 100 $hr^{-1}$.

5. The method of claim 1 wherein said conversion conditions are effective to provide an ethylene/propylene molar product ratio ranging from 0.1 to 7.

* * * * *